United States Patent [19]
Willman et al.

[11] Patent Number: 5,527,821
[45] Date of Patent: Jun. 18, 1996

[54] PHARMACOLOGICALLY ACTIVE ALPHA-[TERTIARY-AMINOMETHYL]-BENZENEMETHANOL DERIVATIVES

[75] Inventors: Nils-Erik Willman, Helsingborg; Bengt C. H. Sjögren, Viken; Lennart G. Nordh, Helsingborg; Gustav L. Persson, Ängelholm, all of Sweden

[73] Assignee: Pharmacia AB, Stockholm, Sweden

[21] Appl. No.: 374,611

[22] PCT Filed: Jul. 20, 1993

[86] PCT No.: PCT/SE93/00635

§ 371 Date: Jan. 18, 1995

§ 102(e) Date: Jan. 18, 1995

[87] PCT Pub. No.: WO94/02442

PCT Pub. Date: Feb. 3, 1994

[30] Foreign Application Priority Data

Jul. 22, 1992 [SE] Sweden ................................. 9202218

[51] Int. Cl.⁶ ...................... A61K 31/395; C07D 207/04
[52] U.S. Cl. ...................... 514/428; 514/258.8; 514/653; 548/574; 544/170; 564/363; 564/365
[58] Field of Search ............................ 548/574; 514/428, 514/238.8, 653; 544/170; 564/363, 365

[56] References Cited

U.S. PATENT DOCUMENTS 4,349,549 9/1982 Roszkowski et al. ...................... 544/71

FOREIGN PATENT DOCUMENTS

| 0103830 | 3/1984 | European Pat. Off. . |
| 213108 | 3/1987 | European Pat. Off. . |
| 0501705 | 9/1992 | European Pat. Off. . |
| 210031 | 5/1984 | Germany . |

OTHER PUBLICATIONS

CA 11329y Substituted Hydroxyethylamines. Mills, p. 1070, 1967.
CA 39280v Substituted . . . amines. Georges Tsatsas et al., p. 3808, 1968.
CA84: 38587 u 2,3—Dihydroxyphenethanolamine as an adrenergic agent. Bartholow et al., p. 14, 1976.
CA89: 157158t 2–Methoxyphenyl ethanolamines, . . . agents, Williams et al., p. 16, 1978.

*Primary Examiner*—Joseph K. McKane
*Attorney, Agent, or Firm*—Birch, Stewart, Kolasch & Birch

[57] ABSTRACT

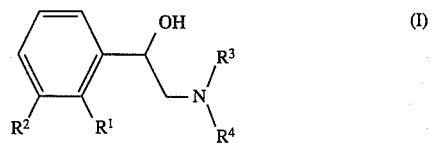

Compounds of formula (I) and their physiologically acceptable salts thereof, their use as therapeutical substances, pharmaceutical compositions containing them, and methods for preparing the compounds.

8 Claims, No Drawings

PHARMACOLOGICALLY ACTIVE ALPHA-[TERTIARY-AMINOMETHYL]-BENZENEMETHANOL DERIVATIVES

This application is a 371 of PCT/SE 93/00635 filed Jul. 20, 1993.

FIELD OF THE INVENTION

The present invention relates to novel α-(tertiaryaminomethyl)-benzanemethanol derivatives having pharmacological properties, and to processes for their preparation. The invention also relates to pharmaceutical compositions containing these derivatives and methods of treatment therewith.

BACKGROUND OF THE INVENTION

Urinary incontinence is a very common disorder in both men and women. Large or smaller amounts of urine are involuntarily expelled from the bladder. There are two main types of urinary incontinence, i.e. urge incontinence and stress incontinence. Very few drugs are available for treatment of the latter type and they have been found to have low efficacy and significant side-effects.

PRIOR ART

DD-A-210 031 discloses a process for the preparation of pharmacologically active 1-aryl-2-aminoethanols. Specifically described are phenylethanolamines which are either unsubstituted or mono-substituted in phenyl ring positions 2 or 4, or tri-substituted in positions 3, 4 and 5.

EP-A-103 830 discloses growth-promoting phenylethanolamine derivatives. No compounds di-substituted in positions 2 and 3 of the phenyl ring are specifically described.

EP-A-213 108 discloses pharmaceutical formulations containing an α- and/or β-sympathicomimetic agent in the form of a phenylethanolamine derivative. The only specific compound mentioned is 1-(3'-hydroxyphenyl)-2-aminoethanol.

U.S. Pat. No. 4,349,549 discloses hypertensively active ω-aryl-ω-hydroxyalkyl-spiropiperidine heterocycles.

SUMMARY OF THE INVENTION

According to the present invention it has been found that a novel class of 2,3-disubstituted-α-(tertiary-aminomethyl)-benzenemethanol derivatives have properties making them suitable for the treatment of disorders related to urinary incontinence, and which novel derivatives have higher efficacy and lower side-effects than the prior art drugs.

In one aspect, the present invention therefore provides novel compounds which may be represented by the general formula I:

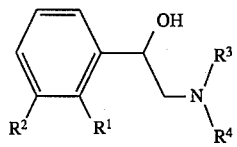

I wherein
$R^1$ is selected from alkyl, alkoxy, alkenyloxy, arylalkoxy, alkylthio and alkenylthio;
$R^2$ is selected from halogen, hydroxy, alkyl, alkoxy, alkenyloxy, alkylthio, alkenylthio, alkylamino, trifluoromethyl, cyano, nitro, alkylsulfinyl, alkylsulfonyl and acyl;
$R^3$ and $R^4$ either independently represent alkyl or alkenyl, or $R^3$ and $R^4$ are interconnected to form a heterocyclic system with the nitrogen atom, optionally containing one or more additional heteroatoms; and physiologically acceptable salts thereof.

In another aspect, the present invention provides the compounds having the general formula I above for therapeutical use, especially as urination controlling agents.

In still another aspect, the present invention provides a method of treating a living body suffering from a disorder related to urinary incontinence, which method comprises the step of administering to the said living body an effective amount of a compound having the general formula I above.

In yet another aspect, the present invention provides a pharmaceutical composition comprising one or more compounds of the general formula I above as the active ingredient, preferably together with a pharmaceutically acceptable carrier and, if desired, other pharmacologically active agents.

In another aspect, the present invention provides the use of the compounds having the general formula I above for the manufacture of a medicament for the treatment of urination control disorders.

In still another aspect, the present invention provides processes for preparing compounds having the general formula I above.

DETAILED DESCRIPTION OF THE INVENTION

In the compounds having the general formula I as defined above, the term alkyl, separately and in combinations such as alkylthio, alkylamino, alkylsulfinyl and alkylsulfonyl, is meant to include straight and branched, saturated hydrocarbon groups. Exemplary alkyl groups are methyl, ethyl, n-propyl, iso-propyl, n-butyl, n-pentyl, n-hexyl.

The term alkenyl, separately and in combinations such as alkenyloxy and alkenylthio, is meant to include straight and branched hydrocarbon groups containing one or more unsaturations. Exemplary alkenyl groups are ethenyl, propenyl, butenyl, pentenyl, hexenyl, methylpropenyl, ethylbutenyl.

The term alkoxy, separately and in combinations such as arylalkoxy, is meant to include straight and branched, saturated alkoxy groups. Exemplary alkoxy groups are methoxy, ethoxy, n-propyloxy, iso-propyloxy, n-butyloxy, n-pentyloxy, n-hexyloxy.

The term alkenyloxy is meant to include straight and branched alkenyloxy groups containing one or more unsaturations. Exemplary alkenyloxy groups are ethenyloxy, propenyloxy, butenyloxy, pentenyloxy, hexenyloxy, methylpropenyloxy, ethylbutenyloxy.

The term aryl, separately and in combinations, is meant to include aromatic systems that are either heterocyclic or only carbon-containing. Exemplary of heterocyclic aromatic systems are thiophene, furan, pyrrole, imidazole, pyrazole, thiazole, isothiazole, oxazole, isoxazole, triazole, pyridine, pyrazine, pyrimidine, pyridazine, benzofuran, isobenzofuran, benzothiazole, benzothiophene, indole, isoindole, oxadiazole, benzoxazole. Exemplary of only carbon-containing aromatic systems are phenyl and naphthyl.

The term acyl is meant to include straight, branched or cyclic, saturated, unsaturated or aromatic acyl groups. Exemplary acyl groups are formyl, acetyl, propionyl, butyryl, succinyl, crotonyl, cinnamoyl, benzoyl.

The term halogen is meant to include fluoro, chloro, bromo and iodo.

$R^1$ is preferably selected from alkoxy and lower alkylthio having 1–5 carbon atoms.

$R^2$ is preferably selected from halogen, alkoxy, alkylthio, trifluoromethyl, cyano, nitro, lower alkylsulfinyl, lower alkylsulfonyl and lower acyl; lower alkyl, lower acyl and lower alkoxy preferably containing 1–5 carbon atoms.

$R^3$ and $R^4$ are preferably, independently, selected from the group consisting of lower alkyl having 1–5 carbon atoms, or $R^3$ and $R^4$, together with the nitrogen atom, form a 5- or 6-membered heterocyclic ring such as pyrrolidine, piperidine, morpholine.

The general formula I includes the enantiomeric and racemic forms. The compounds of formula I which contain salt-forming basic nitrogen atoms may also be in the form of salts suitable for pharmacological use.

The following specific compounds are preferred:

α-[(dimethylamino)methyl]-2-(1-methylethoxy)-3-methyl-benzenemethanol;

3-chloro-α-[(dimethylamino)methyl]-2-ethoxy-benzenemethanol;

α-[(diethylamino)methyl]-3-methoxy-2-(1-methylethoxy)-benzenemethanol;

α-[(dimethylamino)methyl]-3-methoxy-2-(1-methylethoxy)-benzenemethanol;

α-[(dimethylamino)methyl]-3-methoxy-2-(2-propenyloxy)-benzenemethanol;

3-methoxy-2-(1-methylethoxy)-α-pyrrolidinomethyl-benzenemethanol;

3-methoxy-2-(2-propenyloxy)-α-pyrrolidinomethyl-benzenemethanol;

3-chloro-2-(1-methylethoxy)-α-pyrrolidinomethyl-benzenemethanol;

3-chloro-α-[(dimethylamino)methyl]-2-(1-methylethoxy)-benzenemethanol;

3-chloro-α-[(N-ethyl-N-methylamino)methyl]-2-(1-methylethoxy)-benzenemethanol;

3-chloro-α-[(diethylamino)methyl]-2-(1-methylethoxy)-benzenemethanol;

α-[(dimethylamino)methyl]-2-(1-methylethoxy)-3-nitrobenzenemethanol;

3-chloro-α-[(dimethylamino)methyl]-2-(1-methylethylthio)-benzenemethanol;

α-[(dimethylamino)methyl]-3-methoxy-2-(1-methylethylthio)-benzenemethanol;

3-chloro-α-[(dimethylamino)methyl]-2-(methylthio)-benzenemethanol;

α-[(dimethylamino)methyl]-3-methoxy-2-(methylthio)-benzenemethanol;

α-[(dimethylamino)methyl]-2-ethylthio-3-methoxy-benzenemethanol;

α-[(dimethylamino)methyl]-2-(1-methylethoxy)-3-methylthio-benzenemethanol;

α-[(dimethylamino)methyl]-2-(1-methylethoxy)-3-methylsulfonyl-benzenemethanol;

α-[(dimethylamino)methyl]-2-(1-methylethoxy)-3-methylsulfinyl-benzenemethanol.

The compounds having the general formula I may be prepared by conventional methods, and especially according to the following methods a) to e).

Method a:

A compound of the general formula II,

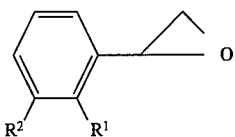

wherein $R^1$ and $R^2$ are as previously defined, is reacted with an amine having the general formula $HNR^3R^4$, wherein $R^3$ and $R^4$ are as previously defined; to form a compound of the general formula I.

Method b:

A compound of the general formula III,

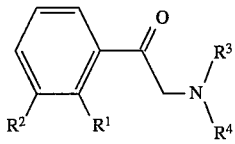

wherein $R^1$, $R^2$, $R^3$ and $R^4$ are as previously defined, is reduced to a compound of the general formula I.

Method c:

A compound having the general formula IV,

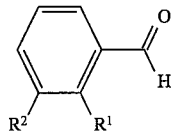

wherein $R^1$ and $R^2$ are as previously defined, is reacted with a reactive derivative of a tertiary amine $NR^3R^4R^5$, wherein $R^3$, $R^4$ and $R^5$ independently are lower alkyl or $R^3$ and $R^4$ together form a saturated ring system, to form a compound having the general formula I.

Method d:

A compound of the general formula V,

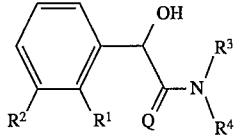

wherein $R^1$, $R^2$, $R^3$ and $R^4$ are as previously defined, and Q is oxygen or sulfur, is reduced to a compound of the general formula I.

Method e:

A compound of the general formula VI,

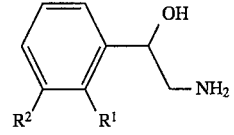

wherein $R^1$ and $R^2$ are as previously defined, is reductively alkylated with an aldehyde to form a compound of the general formula I.

Method a) above (which is illustrated further in Example 1 below) may be carried out by mixing the reagents, or the reagents may be dissolved or suspended in an inert solvent such as an alcohol, e.g., ethanol, water, dimethyl sulfoxide, acetonitrile etc. Mixtures of more than one solvent may be employed. A suitable temperature range for the reaction is between about 20° C. and about 150° C., usually between about 20° C. and about 100° C. The resulting product may be isolated by conventional procedures.

The starting material of formula II may be prepared from compounds of the general formula IV by methods described in Reference (1) in the list of References at the end of the description. The crude epoxide II is preferably directly reacted with the desired amine.

In method b) (which is further illustrated in Example 2 below) the amino ketone III may be reduced by using a conventional reducing agent, such as $LiAlH_4$, $BH_3$—THF, $NaBH_4$ etc., or by catalytic hydrogenation. The process may be carried out in an inert solvent compatible with the reducing agent, e.g. hydrocarbons, ethers, alcohols, carboxylic acids. Mixtures of more than one solvent may also be employed. A suitable temperature range for carrying out the process is between about 20° C. and about 100° C.

The starting material III may be prepared by using general methods as described in Reference (2).

Method c) (which is illustrated further in Example 3 below) may be carried out in an excess of the non-activated amine $NR^3R^4R^5$ or in an inert solvent medium, usually at −70° C. or below. The reactive derivative of the amine may, for example, be $LiCH_2NR^3R^4$, wherein $R^3$ and $R^4$ are lower alkyl groups or together form a saturated ring system.

The reactive amine derivatives can be prepared according to the method described in Reference (3) or from $(n-C_4H_9)_3SnCH_2NR^3R^4$ described in Reference (4). The starting amines, such as $CH_3NR^3R^4$, are known compounds. Compounds having the general formula IV are known compounds or can be prepared by conventional methods as described in Reference (5).

In method d) (which is illustrated further in Example 4 below) the reduction of the tertiary amide (formula V, Q=O) or tertiary thioamide (formula V, Q=S) with a reducing agent to the compound of the general formula I can be performed by using conventional reducing agents, including $LiAlH_4$, $BH_3$—$S(CH_3)_2$, $NaBH_4$—$CoCl_2$, etc. The process may be carried out in an inert organic solvent compatible with the reducing agent, suitably at a temperature between about 20° C. and about 100° C. This reduction may also be performed by catalytic hydrogenation in per se known manner.

The starting material of the general formula V may be prepared from α-hydroxybenzeneacetic acid derivatives by per se known methods or be prepared from compounds of the general formula IV by using methods described in Reference (6).

In method e) (which is illustrated further in Example 5 below) the amino alcohol VI may be reductively alkylated by using a conventional reducing agent, such as $NaBH_3CN$, $NaBH_4$, formic acid, etc., or by catalytic hydrogenation. The process may be carried out in an inert solvent compatible with the reducing agent, e.g. hydrocarbons, ethers, alcohols, carboxylic acids. Mixtures of more than one solvent may also be employed. The process may suitably be performed at a temperature between about 0° C. and about 100° C. The starting material VI may be prepared by using general methods as described in Reference (7).

It is, of course, also possible to prepare compounds having the general formula I above from other compounds within the definition of this general formula, using procedures known per se. As examples of such transformations the following may be mentioned: Free hydroxy groups are, e.g., obtained by removal of acyl groups from carboxylic esters. Lower alkylsulfinyl and lower alkylsulfonyl groups are, e.g., obtained by oxidation of methylthio groups. Primary and secondary amines can be acylated to amides and alkylated to corresponding amines, and amides can be reduced to corresponding amines.

In synthesizing compounds having the general formula I by any of the methods mentioned above, each group of the starting materials involved must be compatible with the process in question or, if necessary protected during one or more reaction steps and then converted to the desired group. Pertinent examples of groups that may be protected are hydroxy, primary amino and secondary amino.

The racemic compounds of the general formula I may be resolved using known methods, such as various resolving acids. Crystallization of a resolving acid salt of compounds of the general formula I may be effected in any suitable conventional inert organic solvent, and preferably at a temperature from the boiling point of the solvent to −20° C. Preferred solvents are ethanol, 1-propanol, 2-propanol and acetone. Water and mixtures of solvents may also be employed.

The separation of racemates can also be achieved by various chromatographic techniques, such as separation of diastereomeric mixtures, separation on chiral stationary phases or with chiral counter ion in the mobile phase.

The resolution of racemates to the individual optical enantiomers is illustrated further in Example 6 below.

All the above described methods, including the resolution of racemates, may optionally be carried out in the presence of a catalyst known to be useful therein.

The compounds of the invention are generally characterized by the pharmacological activity stated above, making them useful for counteracting certain physiological abnormalities in a living human or animal body. Effective quantities of a pharmacologically active compound of the invention may be administered to a living human or animal body in any one of various ways, e.g. orally as in capsules or tablets, parenterally in the form of sterile solutions, suspensions, emulsions, pellet implantation or by pumps. Among routes of parenteral administration are intravenous, sublingual, subcutaneous, intramuscular, intraperitoneal, intradermal, intravesical, intraurethral and intranasal administration. Other modes of administration are vaginal, rectal and topical administrations, e.g. in the form of ointments, suppositories, powders, patches, sprays and intravaginal devices.

Pharmaceutical formulations are usually prepared from a predetermined quantity of one or more of the compounds of the invention. Such formulations may take the form of powders, syrups, suppositories, ointments, solutions, pills, capsules, pellets or tablets, suspensions, emulsions, oil solutions, etc. with or without, but preferably with any one of a large variety of pharmaceutically acceptable vehicles or carriers.

When in a mixture with a pharmaceutical vehicle or carrier, the active ingredient usually comprises from about 0.01 to about 75%, normally about 0.05 to about 15% by weight of the composition. Carriers such as starch, sugar, talc, commonly used synthetic and natural gums, water and the like may be used in such formulations. Binders, such as polyvinylpyrrolidone, and lubricants, such as sodium stearate, may be used to form tablets. Disintegrating agents such as sodium carbonate may also be included in tablets.

Although relatively small quantities of the active materials of the invention, even as low as 0.5 milligram, may be used in cases of administration to subjects having a relatively low body weight, unit dosages are preferably 2 milligrams or above, and preferably 10, 20, 50 or 100 milligrams, or even higher depending, of course, upon the subject treated and the particular result desired, as will be apparent to one skilled in the art. Broader ranges would be from 1 to 1000 milligrams per unit dose.

The present compounds of formula I may thus be administered in a quantity of 1 to 1000 milligrams, preferred ranges being 2 to 250 milligrams per day per subject or patient divided into one to four doses over a suitable period and depending upon the subject and the type of subject being treated.

EXAMPLES

The following examples are intended to illustrate but not to limit the scope of the invention, the compounds specifically named, however, being of particular interest for the intended purposes. These compounds are designated by numbers in the Examples where their preparations are described and where their systematic names are given. The compounds are later on referred to by a number code, a:b, where "a" means the number of the example, in which the preparation of the compound in question is described, and "b" refers to the order of the compounds prepared according to that example. Thus, compound 1:2 means the second compound prepared according to Example 1.

The structures of the compounds prepared are confirmed by NMR and elementary or titrimetric analyses. The NMR data were recorded using a BRUKER 250 MHZ instrument. Elementary analyses were performed using a Carlo Erba Elementar Analyzer Mod. 1106. Melting points, when given, were determined on a Mettler FF apparatus and are uncorrected.

Example 1

2-[3-methyl-2-(1-methylethoxy)phenyl]oxirane (1.92 g, 0.01 mole) is added to dimethylamine (1.35 g, 0.03 mole) at −15° C. in a pressure vessel and is allowed to warm up to room temperature with stirring during 8 h. It is then kept at ambient temperature for 40 h. After cooling, the excess of the amine is evaporated and purified by chromatography on silica gel using toluene:methanol (containing 20% by weight of ammonia), 9:1. The desired fraction is, if necessary, isolated as a suitable salt.

1. α-[(Dimethylamino)methyl]-2-(1-methylethoxy)-3-methyl-benzenemethanol, hydrochloride, m.p. 104° C.

In essentially the same manner the following compounds are obtained from the corresponding starting materials:

2. 3-Chloro-α-[(dimethylamino)methyl]-2-ethoxy-benzenemethanol, hydrochloride, m.p. 135° C.
3. α-[(Diethylamino)methyl]-3-methoxy-2-(1-methylethoxy)-benzenemethanol, hydrogen oxalate, m.p. 95° C.
4. α-[(Dimethylamino)methyl]-3-methoxy-2-(1-methylethoxy)-benzenemethanol, hydrogen oxalate, m.p. 126° C.
5. 3-Methoxy-2-(1-methylethoxy)-α-pyrrolidinomethyl-benzenemethanol, hydrochloride, m.p. 213° C.
6. 3-Methoxy-2-(1-methylethoxy)-α-morpholinomethyl-benzenemethanol, hydrochloride, m.p. 160° C.
7. 3-Chloro-2-(1-methylethoxy)-α-pyrrolidinomethyl-benzenemethanol, hydrogen oxalate, m.p. 128° C.
8. 3-Methoxy-2-(1-propenyloxy)-α-pyrrolidinomethyl-benzenemethanol, hydrogen oxalate, m.p. 103° C.
9. 3-Chloro-α-[(dimethylamino)methyl]-2-(1-methylethoxy)-benzenemethanol, hydrochloride, m.p. 120° C.
10. 3-Chloro-α-[(diethylamino)methyl]-2-(1-methylethoxy)-benzenemethanol, hydrogen oxalate, m.p. 91° C.
11. 3-Chloro-α-[(N-ethyl-N-methylamino)methyl]-2-(1-methylethoxy)-benzenemethanol, hydrochloride, m.p. 127° C.
12. α-[(Dimethylamino)methyl]-2-(1-methylethoxy)-3-nitro-benzenemethanol, hydrochloride, m.p. 133° C.
13. 3-Chloro-α-[(dimethylamino)methyl]-2-(1-methylethylthio)-benzenemethanol, hydrochloride, m.p. 141° C.
14. α-[(Dimethylamino)methyl]-3-methoxy-2-(1-methylethylthio)-benzenemethanol, hydrochloride, m.p. 141° C.
15. α-[(Dimethylamino)methyl]-3-methoxy-2-(2-propenyloxy)-benzenemethanol, hydrogen oxalate, m.p. 80° C.
16. α-[(Dimethylamino)methyl]-2,3-di-(1-methylethoxy)-benzenemethanol, base, m.p. 44° C.
17. α-[(Dimethylamino)methyl]-3-methoxy-2-[(3-methyl-2-butenyl)oxy]-benzenemethanol (oil).

Example 2

To a solution of 2-(dimethylamino)-1-(3-chloro-2-ethoxyphenyl)ethanone, hydrochloride (2.25 g, 0.0081 mole) in methanol (50 ml) and water (15 ml) is added with stirring and cooling (−5° C.) sodium borohydride (0.65 g, 0.0171 mole) in portions. After stirring at ambient temperature for 2 h, 10 ml of 2N hydrochloric acid is added. The mixture is concentrated under reduced pressure to remove methanol, diluted with water and made alkaline with concentrated ammonium hydroxide. After extraction of the mixture with ether, the ether layer is dried over anhydrous sodium sulfate. The desired product is isolated as the hydrochloride (1) below and recrystallized from 2-propanol:ether.

1. 3-Chloro-α-[(dimethylamino)methyl]-2-ethoxy-benzenemethanol, hydrochloride, m.p. 135° C. (Compound 2:1=compound 1:2).

In essentially the same manner the following compound is obtained from the corresponding starting material:

2. 3-Chloro-α-[(dimethylamino)methyl]-2-(1-methylethoxy)-benzenemethanol, hydrochloride, m.p. 120° C. (Compound 2:2=compound 1:9).

Example 3

Sec. butyllithium (1.3M solution in hexene) (0.77 ml, 0.01 mole) is added dropwise under nitrogen at −78° C. to a stirred mixture of 8 ml of trimethylamine and potassium t-butoxide (1.12 g, 0.01 mole). The mixture is stirred at 0° C. for 1 h and cooled to −78° C. Thereafter, 35 ml of 0.3M solution of lithium bromide in ether is added dropwise. The mixture is stirred for 1 h at 0° C. and cooled to −78° C., and 3-methoxy-2-(1-methylethoxy)-benzaldehyde (1.55 g, 0.008 mole) in 10 ml of ether is added at −78° C. The reaction mixture is allowed to stay at room temperature over night and poured into ice-water, acidified to pH 3 and extracted twice with ether. The ether extract is washed with water and dried over anhydrous sodium sulfate. The desired product is isolated as the oxalate (1) below and recrystallized from propanol:ether.

1. α-[(Dimethylamino)methyl]-3-methoxy-2-(1-methylethoxy)-benzenemethanol, hydrogen oxalate, m.p. 126° C. (Compound 3:1=compound 1:4).

In essentially the same manner the following compound is obtained from the corresponding starting material:

2. 3-Chloro-α-[(dimethylamino)methyl]-2-(1-methylethoxy)-benzenemethanol, hydrochloride, m.p. 120° C. (Compound 3:2=compound 1:9).

Example 4

A solution of N,N-dimethyl-α-hydroxy-3-methoxy-2-(1-methylethoxy)-benzeneethanethioamide (2.87 g, 0.01 mole) in 20 ml of anhydrous THF is added to a stirred suspension of lithium aluminium hydride (1.5 g) in 15 ml of anhydrous THF under a nitrogen atmosphere. The mixture is refluxed for 18 h and cooled. Destruction of the excess of lithium aluminium hydride is completed by cautious dropwise addition of 1.5 ml of water followed by 2.3 ml of 15% aqueous sodium hydroxide solution and subsequent addition of 4.5 ml of water. Stirring is continued until a granular white precipitate is formed. Filtration yields a clear solution. THF is removed under reduced pressure and the residue is dissolved in ether. The desired product is isolated as hydrogen oxalate and recrystallized from ethyl acetate.

α-[(Dimethylamino)methyl]-3-methoxy-2-(1-methylethoxy)-benzenemethanol, hydrogen oxalate, m.p. 126° C. (Compound 4:1=compound 1:4).

Example 5

α-Aminomethyl-3methoxy-2-(1-methylethoxy)-benzenemethanol, (9 g, 0.04 mole), formic acid (98–100%) (9.2 g, 0.2 mole) and formaldehyde (37%) (7.2 g, 0.0088 mole) is refluxed for 4 h. Then 3.4 ml of concentrated hydrochloric acid is added and the formic acid and any excess formaldehyde are removed under reduced pressure. The residue is dissolved in water and made alkaline (pH>11) by the addition of 25% aqueous sodium hydroxide, and the mixture is extracted twice with ether and isolated as the hydrogen oxalate.

α-[(Dimethylamino)methyl]-3-methoxy-2-(1-methylethoxy)-benzenemethanol, hydrogen oxalate, m.p. 126° C. (Compound 5:1=compound 1:4).

Example 6

The following examples illustrate the resolution of racemates according to the invention:

The racemic 3-chloro-α-[(dimethylamino)methyl]-2-(1-methylethoxy)-benzenemethanol (19.35 g, 0.075 mole) and di-O,O'-p-toluoyl-L-tartaric acid (30.3 g, 0.075 mole) are mixed and the product crystallized from 125 ml of abs. ethanol and 175 ml of water. The mixture is left over night at +4° C. The precipitated salt is collected by filtration and washed with ethanol-water 1:1. The product, 42.71 g, is recrystallized twice from 50% ethanol and converted via the base to the hydrochloride of (−)(-3-chloro-α-[(dimethylamino)methyl]-2-(1-methylethoxy)-benzenemethanol. Yield 6.6 g. M.p. 99° C. $[\alpha]_D^{25}=-52.4°$ (C=1% in ethanol). (Compound 6:1)

The mother liquors from the two first crystallizations are concentrated together to almost dryness on a rotary evaporator. The residue is made alkaline with 2M sodium hydroxide solution and extracted with ether. The ether layer is evaporated (14.7 g, 0.057 mole) and crystallized with di-O,O'-p-toluoyl-D-tartaric acid (21.9 g, 0.057 mole) from 195 ml of 50% ethanol. The product is recrystallized three times from 50% ethanol. The product (19.5 g) is converted via the base to the hydrochloride of (+)-3-chloro-α-[(dimethylamino)methyl]-2-(1-methylethoxy)-benzenemethanol. Yield 7.2 g. M.p. 98° C. $[\alpha]_D^{25}=+50.9°$. (C=1% in ethanol). (Compound 6:2)

The racemic α-[(dimethylamino)methyl]-3-methoxy-2-(1-methylethoxy-benzenemethanol (253.0 g, 1 mole) and di-O,O'-p-toluoyl-D-tartaric acid (386.3 g, 1 mole) are mixed and the product crystallized from ethanol-water 6:4 (765 ml). After 20 hours at room temperature, the temperature is gradually decreased at 10° C. The precipitated salt is collected by filtration and washed with ethanol-water 1:1 (2×60 ml) and ethanol-water 6:4 (2×60 ml) and dried in vacuum. The product, 205 g, is recrystallized twice from ethanol-water 6:4, and converted to the base, (+)-α-[(dimethylamino)methyl]-3-methoxy-2-(1-methylethoxy)-benzenemethanol. Yield 51 g. M.p. 49.2° C. $[\alpha]_D^{25}=+52°$ (C=1% in ethanol). (Compound 6:3)

The mother liquors from the two first crystallizations are concentrated together to almost dryness on a rotary evaporator. The residue is made alkaline with 2M sodium hydroxide solution and extracted with ether. The ether layer is evaporated. 87 g (0.343 mole) of the base are crystallized with di-O,O-p-toluoyl-L-tartaric acid (132.8 g, 0.343 mole) from ethanol:water 6:4, 231 ml. The precipitated salt is collected by filtration and washed with ethanol:water 1:1 (2×20 ml) and ethanol:water 6:4 (2×20 ml) and dried in vacuum. The product, 70.3 g, is recrystallized twice from ethanol:water 6:4 and converted to the base, (−)-α-[(dimethylamino)methyl]-3-methoxy-2-(1-methylethoxy)-benzenemethanol. Yield 17.5 g. M.p. 49.1° C. $[\alpha]_D^{25}=-52°$ (C=1% in ethanol). (Compound 6:4).

Example 7

| Manufacturing process for tablets of 20 mg. Model batch for 1000 tablets | | | |
|---|---|---|---|
| I | Active Compound, mesh* 70 | | 20 g |
| | Lactosum, Ph. Nord | | 210 g |
| | Amylum maidis, Ph. Nord | | 75 g |
| II | Kollidon 25 B.A.S.F. | | 3.5 g |
| | Aqua purificata | | q.s. |
| III | Talcum, Ph. Nord | | 15 g |
| | Magnesii stearas, Ph. Nord. | | 1.5 g |
| Weight of 1000 tablets | | | 325 g |
| Weight of 1 tablet: 325 mg | | | |

*The mesh standard is according to the international system of code DIN 4189/1968.

Punch: 10.5 mm round, flat scored, bevel-edged.

Mix the screened substances I thoroughly and then moisten with II, whereupon the mixture is granulated through a stainless sieve No. 10 (mesh 25). Dry the granulate in an oven at a maximum temperature of 40° C., then repeat sieving through sieve No. 10. Add the substances under III and mix thoroughly. Punch tablets with a gross weight of about 325 mg.

Example 8

| Suspension for injection 20 mg/ml | |
|---|---|
| Active compound, mesh 100 | 20 mg |
| Sodium Chloride | 8 mg |
| Carboxy methylcellulose | 1 mg |
| Benzyl alcohol | 1 mg |
| Distilled water to make | 1 ml |

Example 9

| Oral suspension 5 mg/ml | |
|---|---|
| Active compound, mesh 100 | 20 mg |
| Sorbitol | 600 mg |
| Flavouring compound | q.s. |

-continued

| Colour | q.s. |
|---|---|
| Water to make | 1 ml |

Example 10

| Suppositoria of 25 mg | |
|---|---|
| Active compound | 25 mg |
| Cocoa butter | q.s. |

Example 11

| Ointment 2% | |
|---|---|
| Active compound | 2 g |
| Triethanolamine | 1 g |
| Glycerol | 7 g |
| Cetanol | 2.5 g |
| Lanolin | 2.5 g |
| Stearic acid | 20 g |
| Sorbitan monooleate | 0.5 g |
| Sodium hydroxide | 0.2 g |
| Methyl paraben | 0.3 g |
| Propyl paraben | 0.1 g |
| Ethanol | 0.9 g |
| Water to make | 100 g |

Example 12

| Capsules of 10 mg | |
|---|---|
| Active compound | 10 mg |
| Magnesium stearate | 2 mg |
| Talcum | 188 mg |

The substances are mixed and filled in capsules.

Example 13

| 20 mg sterile powder to be dissolved in water for injection | |
|---|---|
| Water-soluble Active Compound | 10 mg |
| Sodium chloride | 4 mg |
| Methyl paraben | 0.7 mg |
| Propyl paraben | 0.3 mg |

The substances are dissolved in distilled water. The solution is dispensed in vials and freeze-dried.

Example 14

| Injectable solution 20 mg/ml | |
|---|---|
| Water-soluble Active Compound | 20 mg |
| Ascorbic acid | 1 mg |
| Sodium bisulfite | 1 mg |
| Sodium chloride | 6 mg |
| Methyl paraben | 0.7 mg |
| Propyl paraben | 0.3 mg |
| Distilled water to make | 1 ml |

In the foregoing Examples 7–14 relating to compositions, the Active Compounds are those covered by the general formula I above or their addition salts with pharmaceutically acceptable inorganic or organic acids. Water-soluble Active Compounds are such addition salts or salts with a pharmaceutically acceptable inorganic or organic cation. Also, it is to be noted that two or more Active Compounds of the invention may be used in combination in the composition illustrated, and also, if desired, in combination with other pharmacologically active agents.

The compounds according to the invention are also expected to be effective by instillation in the urinary bladder in doses of 0.0005 to 1 mg/kg body weight. However, it will be understood that the amount of compound actually administered will be determined by a physician, in the light of the relevant circumstances including the condition to be treated, the chosen route of administration, the age, weight and response of the individual patient and the severity of the patient's symptoms, and therefore the above dosage ranges are not intended to limit the scope of the invention in any way. As used herein the terms "pharmaceutical formulations" embrace compositions and ingredients for both human and veterinary use.

The following pharmacological data illustrate the effect of a number of potent and selective substances in comparison with a classical α-adrenoceptor stimulating substance, phenylpropanolamine.

Effects on the Isolated Rabbit Urethra and Portal Vein

Female rabbits weighing 2.5–3.0 kg were sacrificed and exsanguinated. The urethra and portal vein were dissected out and suspended in organ baths containing oxygenated Krebs solution at 37° C. Two rings of urethra (4 mm broad) and two longitudinal strips of the portal vein were used. The basal tension was adjusted to about 10 mN after an equilibration time of 60 minutes. Isometric tension was recorded via a force transducer (Statham FT03) and registered on a Grass polygraph model 7.

Submaximum concentrations of noradrenaline ($6 \times 10^{-5}$M) were used to achieve reference contractions.

The test substances were added cumulatively (12 concentrations) until a maximum response was obtained. The results are summarized in Table 1 below.

Effects on Urethral and Blood Pressure in Anaesthetized Rabbits

Rabbits, weighing 2.5–3 kg, were anaesthetized by pentobarbitone (initially 40 mg/kg i.v. and for maintenance anaesthesia 10 mg/kg, h). For recording of urethral pressure a catheter (Dog cath nr 6.) was inserted into the urethra and placed at the point of highest pressure. The basal urethral pressure was approximately 10 cm $H_2O$. The blood pressure was recorded via a catheter (PP50) inserted into a femoral artery. Substances were injected intravenously into a catheter in a femoral vein. The continuous intravenous infusion of pentobarbitone kept the depth of anesthesia at a constant level through the experiment. Three consecutive noradrenaline injections (0.025 µg/kg i.v.) were given initially to constitute reference responses. Repeated intravenous injections of different doses of the same test compound were given in a randomized manner. The results are summarized in Table 1 below. The data clearly show that the compounds described have a very high selectivity for the urethra in comparison with their effects on blood vessels and blood pressure. In other pharmacological experiments (not described here) it was also shown that the described compounds had no or minimal effect on other organs, such as for example the urinary bladder, central nervous system, intestine, vas deferens etc.

TABLE 1

EC50 = effective concentration inducing a half maximum contraction
NA = noradrenaline, PPA = phenylpropanolamine

| Compound | Urethra, in vitro | | Portal vein, in vitro | | Max. urethral pressure in vivo, in % of NA-max | Blood pressure; max change, in % |
|---|---|---|---|---|---|---|
| | Max. contraction % of NA-max | EC50-value in M | Max. contraction % of NA-max | EC50 value in M | | |
| Noradrenaline | 100 | $1.6 \times 10^{-5}$ | 100 | $5.3 \times 10^{-6}$ | 100 | |
| PPA | 60 | $2.0 \times 10^{-4}$ | 67 | $7.0 \times 10^{-5}$ | 99 | 72 |
| 9 | 79 | $1.1 \times 10^{-5}$ | 22 | $6.0 \times 10^{-5}$ | 192 | 14 |
| 2 | 105 | $1.8 \times 10^{-5}$ | 22 | $6.7 \times 10^{-6}$ | 123 | 9 |
| 11 | 100 | $5.3 \times 10^{-6}$ | 54 | $4.5 \times 10^{-6}$ | 210 | 34 |
| 1 | 85 | $2.4 \times 10^{-5}$ | 47 | $2.4 \times 10^{-5}$ | | |
| 10 | 81 | $1.2 \times 10^{-5}$ | 28 | $1.1 \times 10^{-5}$ | | |
| 7 | 73 | $1.2 \times 10^{-5}$ | 14 | $4.1 \times 10^{-5}$ | 189 | −3 |
| 4 | 95 | $5.7 \times 10^{-6}$ | 35 | $8.7 \times 10^{-5}$ | 211 | 10 |
| 3 | 105 | $6.6 \times 10^{-6}$ | 11 | $1.3 \times 10^{-4}$ | 131 | −2 |
| 8 | 52 | $1.9 \times 10^{-4}$ | 0 | 0 | | |
| 6:1 | 69 | $2.1 \times 10^{-5}$ | 9 | — | | |
| 6:2 | 107 | $4.5 \times 10^{-6}$ | 15 | $1.7 \times 10^{-5}$ | | |
| 15 | 104 | $4.7 \times 10^{-5}$ | 11 | $9.0 \times 10^{-5}$ | | |
| 6:3 | 106 | $6.5 \times 10^{-6}$ | 34 | $1.2 \times 10^{-4}$ | 288 | 14 |
| 6:4 | 88 | $6.1 \times 10^{-5}$ | 8 | — | 150 | 11 |
| 12 | 80 | $1.1 \times 10^{-5}$ | 18 | $1.7 \times 10^{-5}$ | | |
| 13 | 45 | $7.7 \times 10^{-5}$ | 4 | — | | |
| 14 | 67 | $1.1 \times 10^{-5}$ | 5 | — | | |
| 5 | 68 | $1.1 \times 10^{-4}$ | 6 | — | | |

REFERENCES

1. A. S. Rao, et al., Tetrahedron 39 (1983), 2323; D. S. Matteson, Tetrahedron Lett. 27 (1986), 795, and references cited therein.
2. Houben-Weyl: Methoden der organischen Chemie, Ketone III 7/2c, 2253, and references cited therein.
3. H. Ahlbrecht, et al., Tetrahedron Lett. 24 (1984), 1353.
4. J. P. Quintard, et al., Synthesis (1984), 495.
5. Houben-Weyl: Methoden der organischen Chemie, Aldehyde E3, 767, Sauerstoffverbindungen II 7/1, 537, and references cited therein.
6. P. Beak, Chemical Reviews 78 (1978), 275; Chemical Reviews 84 (1984), 471, and references cited therein.
7. Comprehensive Organic Chemistry (1979), Vol. 2, 94, and references cited therein.

We claim:

1. A compound of the general formula I

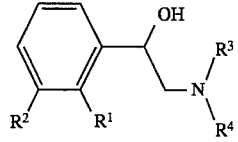

wherein
$R^1$ is selected from alkyl, alkoxy, alkenyloxy, arylalkoxy, alkylthio and alkenylthio;
$R^2$ is selected from halogen, hydroxy, alkyl, alkoxy, alkenyloxy, alkylthio, alkenylthio, alkylamino, trifluoromethyl, cyano, nitro, alkylsulfinyl, alkylsulfonyl and acyl;
$R^3$ and $R^4$ either independently represent alkyl or alkenyl, or $R^3$ and $R^4$ are interconnected to form a heterocyclic system with the nitrogen atom, optionally containing one or more additional heteroatoms; and physiologically acceptable salts thereof.

2. A compound according to claim 1, wherein
$R^1$ is selected from alkoxy and lower alkylthio having 1–5 carbon atoms,
$R^2$ is selected from halogen, alkoxy, alkylthio, trifluoromethyl, cyano, nitro, lower alkylsulfinyl, lower alkylsulfonyl and lower acyl, lower alkyl, lower acyl and lower alkoxy containing 1–5 carbon atoms, and
$R^3$ and $R^4$ are independently selected from lower alkyl having 1–5 carbon atoms, or $R^3$ and $R^4$, together with the nitrogen atom, form a 5- or 6-membered heterocyclic ring.

3. A compound according to claim 1 selected from:
α-[(dimethylamino)methyl]-2-(1-methylethoxy)-3-methyl-benzenemethanol;
3-chloro-α-[(dimethylamino)methyl]-2-ethoxy-benzenemethanol;
α-[(diethylamino)methyl]-3-methoxy-2-(1-methylethoxy)-benzenemethanol;
α-[(dimethylamino)methyl]-3-methoxy-2-(1-methylethoxy)-benzenemethanol;
α-[(dimethylamino)methyl]-3-methoxy-2-(2-propenyloxy)-benzenemethanol;
3-methoxy-2-(1-methylethoxy)-α-pyrrolidinomethyl-benzenemethanol;
3-methoxy-2-(2-propenyloxy)-α-pyrrolidinomethyl-benzenemethanol;
3-chloro-2-(1-methylethoxy)-α-pyrrolidinomethyl-benzenemethanol;
3-chloro-α-[(dimethylamino)methyl]-2-(1-methylethoxy)-benzenemethanol;
3-chloro-α-[(N-ethyl-N-methylamino)methyl]-2-(1-methylethoxy)-benzenemethanol;
3-chloro-α-[(diethylamino)methyl]-2-(1-methylethoxy)-benzenemethanol;
α-[(dimethylamino)methyl]-2-(1-methylethoxy)-3-nitro-benzenemethanol;

3-chloro-α-[(dimethylamino)methyl]-2-(1-methylethylthio)-benzenemethanol;

α-[(dimethylamino)methyl]-3-methoxy-2-(1-methylethylthio)-benzenemethanol;

3-chloro-α-[(dimethylamino)methyl]-2-(methylthio)-benzenemethanol;

α-[(dimethylamino)methyl]-3-methoxy-2-(methylthio)-benzenemethanol;

α-[(dimethylamino)methyl]-2-ethylthio-3-methoxy-benzenemethanol;

α-[(dimethylamino)methyl]-2-(1-methylethoxy)-3-methylthio-benzenemethanol;

α-[(dimethylamino)methyl]-2-(1-methylethoxy)-3-methylsulfonyl-benzenemethanol;

α-[(dimethylamino)methyl]-2-(1-methylethoxy)-3-methylsulfinyl-benzenemethanol;

and physiologically acceptable salts thereof.

4. A compound according to any one of claims 1 to 3 for use as a therapeutically active substance.

5. A method of treating a living body suffering from a disorder related to urinary incontinence, which method comprises the step of administering to said living body an effective amount of a compound according to any one of claims 1 to 3.

6. A pharmaceutical composition comprising one or more compounds according to any one of claims 1 to 3, optionally together with a pharmaceutically acceptable carrier.

7. A method for preparing a compound of formula I as defined in claim 1, which comprises a) reacting a compound having the general formula IV,

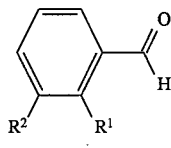

IV wherein $R^1$ and $R^2$ are as defined in claim 1, with a reactive derivative of a tertiary amine $NR^3R^4R^5$, wherein $R^3$, $R^4$ and $R^5$ independently are lower alkyl or $R^3$ and $R^4$ together form a saturated ring system; or b) reducing a compound of the general formula V,

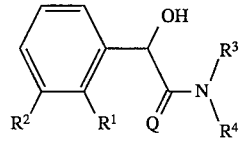

V wherein $R^1$, $R^2$, $R^3$ and $R^4$ are as defined in claim 1, and Q is oxygen or sulfur; or c) reductively alkylating a compound of the general formula VI,

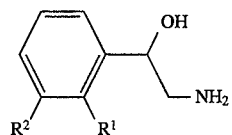

VI wherein $R^1$ and $R^2$ are as defined in claim 1, with an aldehyde; or d) converting a compound of formula I as defined in claim 1 to another compound of formula I;

and, if desired, separating a racemate obtained into optical isomers and/or forming an acid addition salt with an organic or inorganic acid.

8. A compound of claim 3 wherein said compound is α-[(dimethylamino)methyl]-3-methoxy-2-(1-methylethoxy)-benzenemethanol.

* * * * *